US008352036B2

(12) United States Patent
DiMarco et al.

(10) Patent No.: US 8,352,036 B2
(45) Date of Patent: Jan. 8, 2013

(54) RESPIRATORY MUSCLE ACTIVATION BY SPINAL CORD STIMULATION

(75) Inventors: Anthony F. DiMarco, Solon, OH (US); Krzysztof E. Kowalski, Strongsville, OH (US)

(73) Assignee: Anthony DiMarco, Solon, OH (US)

( * ) Notice: Subject to any disclaimer, the term of this patent is extended or adjusted under 35 U.S.C. 154(b) by 591 days.

(21) Appl. No.: 12/355,986

(22) Filed: Jan. 19, 2009

(65) Prior Publication Data

US 2010/0185253 A1 Jul. 22, 2010

(51) Int. Cl.
*A61N 1/18* (2006.01)
(52) U.S. Cl. .......................................... 607/42
(58) Field of Classification Search ............ 607/42
See application file for complete search history.

(56) References Cited

U.S. PATENT DOCUMENTS

| 4,830,008 | A | | 5/1989 | Meer |
| 5,058,584 | A | | 10/1991 | Bourgeois |
| 5,540,732 | A | | 7/1996 | Testerman |
| 5,911,218 | A | * | 6/1999 | DiMarco ................ 128/200.24 |
| 5,999,855 | A | | 12/1999 | DiMarco |
| 6,233,488 | B1 | * | 5/2001 | Hess .............................. 607/58 |
| 7,047,079 | B2 | * | 5/2006 | Erickson ....................... 607/46 |
| 7,840,270 | B2 | * | 11/2010 | Ignagni et al. ................. 607/42 |
| 2004/0088015 | A1 | | 5/2004 | Casavant et al. |

OTHER PUBLICATIONS

Dimarco, Anthony F, et al.; "Effects of Diaphragm Activation on Airway Pressure Generation During Lower Thoracic Spinal Cord Stimulation"; Respiratory Physiology & Neurobiology; 2007; pp. 102-107; vol. 190; Elsevier.
Brown, Robert, et al.; "Respiratory Dysfunction and Management in Spinal Cord Injury"; The Science Journal of the American Association for Respiratory Care; Aug. 2006; pp. 853-870; vol. 51, Issue No. 8; Irving, TX.
Butler, J.E., et al.; "Discharge Properties and Recruitment of Human Diaphragmatic Motor Units During Voluntary Inspiratory Tasks"; Journal of Physiology; pp 907-920; 1999.
Gandevia, Simon C., et al.; "Spatial Distribution of Inspiratory Drive to the Parasternal Intercostal Muscles in Humans"; The Physiological Society; 2006; pp. 263-275.
Detroyer, Andre, et al.; "Distribution of Inspiratory Drive to the External Intercostal Muscles in Humans"; The Physiological Society; 2002; pp. 943-954.
Gandevia, Simon C., et al.; "Effects of Increased Ventilatory Drive on Motor Unit Filing Rates in Human Inspiratory Muscles"; American Journal of Respiratory and Critical Care Medicine of the American Thoracic Society; Apr. 5, 1999; pp. 1598-1603; vol. 160; New York.
International Search Report for PCT International Patent Application No. PCT/US2010/000123, Jan. 19, 2010.
International Written Opinion for PCT International Patent Application No. PCT/US2010/000123, Jan. 19, 2010.

* cited by examiner

*Primary Examiner* — Scott Getzow
*Assistant Examiner* — Amanda Patton
(74) *Attorney, Agent, or Firm* — Curatolo Sidoti Co., LPA; Salvatore A. Sidoti

(57) ABSTRACT

A method of electrically stimulating the inspiratory muscles in a subject is provided. The method includes positioning one or more electrodes at one or more levels of the upper thoracic spinal cord of the subject and operating the electrode to deliver high frequency electrical stimulation to the spinal cord tracts at the level or levels. The high frequency electrical stimulation of the spinal cord results in the coordinated activation of the diaphragm, intercostal muscles, and accessory muscles in the subject to effect artificial ventilation in the subject.

38 Claims, 13 Drawing Sheets

FIG.11
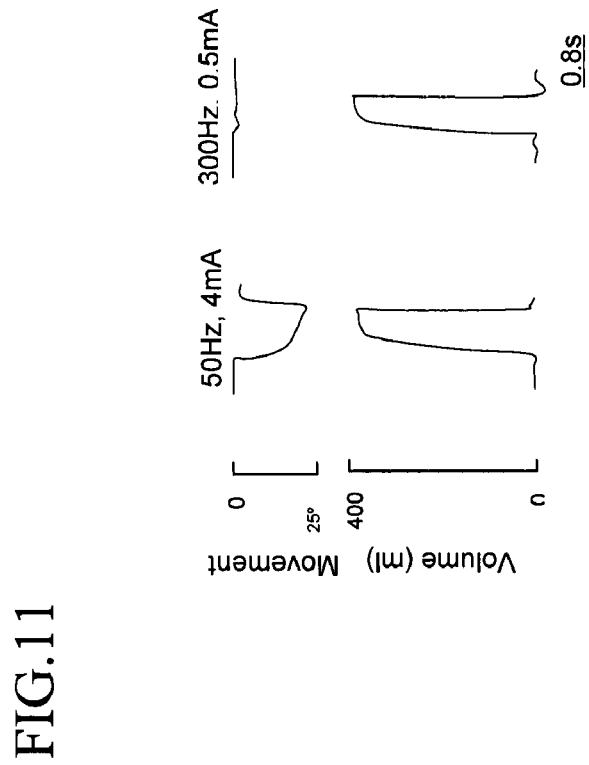
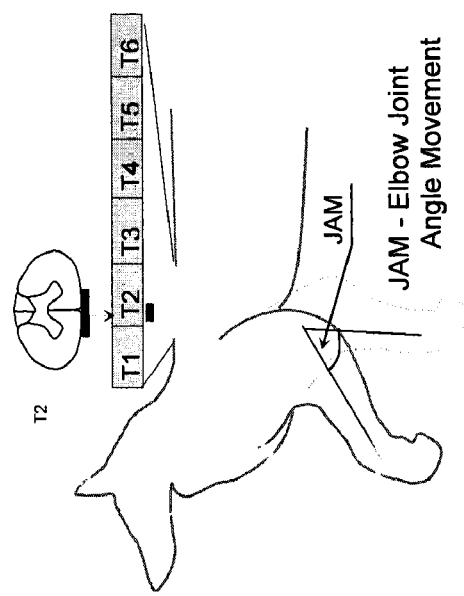

RESPIRATORY MUSCLE ACTIVATION BY SPINAL CORD STIMULATION

TECHNICAL FIELD

Disclosed is a method for stimulating the respiratory muscles of a subject by high frequency electrical stimulation of the spinal cord. More particularly, the method is directed to activation of the diaphragm, intercostal and accessory muscles of a subject, either alone or in combination, by high frequency stimulation of the spinal cord to effect artificial ventilation in the subject.

BACKGROUND

There are more than 200,000 patients with spinal cord injury in the United States, with about 11,000 new injuries occurring each year. Within this group, about 40 to about 50 percent of these patients have cervical spinal cord lesions resulting in tetraplegia. Patients with low cervical spinal cord lesions with preserved connections to the phrenic nerve motorneuron pools are able to breathe spontaneously without artificial ventilatory assistance. With high cervical cord lesions, however, there is disruption of the bulbospinal respiratory pathways which synapse with inspiratory motorneuron pools, resulting in paralysis of the diaphragm and intercostal muscles, the major muscles of inspiration. With only the accessory muscles of respiration remaining, there is insufficient inspiratory muscle force generating capacity to maintain ventilatory requirements and blood gas homeostasis. Consequently, these patients are generally dependent upon mechanical ventilatory support. Although most patients experience subsequent improvement in neurologic function and are eventually able to breathe spontaneously, about 5 percent of this group will remain dependent upon some form of artificial ventilatory support system for the remainder of their life. Many spinal cord injuries occur in young individuals whose life expectancies have increased substantially due to improvements in medical care. Therefore, many ventilator dependent patients can be expected to live a near normal life span.

While mechanical ventilation maintains basic physiologic needs, most patients experience multiple handicaps. These handicaps include reduced mobility, difficulty with bodily movement, difficulty with speech, significant mental anxiety related to possible disconnection from the ventilator, embarrassment associated with the appearance and sound of the ventilator that attracts attention in social settings, reduced sensation of smell, and atelectasis. Furthermore, mechanical ventilation requires a tracheostomy and is associated with the development of frequent respiratory tract infections often necessitating hospitalization.

In certain spinal cord injuries, the spinal cord below the level of the lesion generally remains intact. The motor pathways in this portion of the spinal cord therefore are amenable to restorative stimulation techniques. Functional electrical stimulation (FES) encompasses a variety of methods to activate motor nerves as a means of restoring function to paralyzed muscles. Bilateral phrenic nerve pacing (PNP), a form of FES, was introduced more than two decades ago. According to this technique, artificial ventilation is produced by rhythmic contraction of the diaphragm such that ventilator dependent tetraplegics can be maintained comfortably without mechanical assist devices. Preserved function of both phrenic nerves is necessary to achieve full-time ventilatory support via PNP. It has been reported that unilateral PNP has a low success rate due to inadequate inspired volume production and therefore PNP is not advised in patients with only unilateral diaphragm function. Obviously, tetraplegics with damage to the phrenic motorneuron pools or phrenic nerves bilaterally are not candidates for PNP.

It is estimated that as many as about 30 to about 40 percent of ventilator dependent tetraplegics have phrenic nerve damage. Conventional PNP techniques require the placement of electrodes directly on the phrenic nerves, carries the risk of phrenic nerve injury and usually requires a thoracotomy, a major surgical procedure with associated risks, required in-patient hospital stay and high cost. PNP may also be accomplished via placement of intramuscular diaphragm electrodes near the phrenic nerve motor point (intramuscular PNP) via laparoscopy, thereby eliminating the need for more invasive thoracotomy and prolonged hospitalization, and therefore significantly reducing cost. This technique essentially eliminates the risk of phrenic nerve injury. This PNP technique also requires preserved bilateral function of the phrenic nerves.

Despite careful pre-surgical screening of patients to ensure phrenic nerve viability, only about 50 percent of patients achieve full-time ventilatory support with either conventional PNP or intramuscular PNP. Nonetheless, PNP is successful in achieving significant ventilator free time (12-15 hours/day) in about 80% of patients. A significant number (10-15%) however achieve <5 hours/day of ventilator free time. The lack of success in achieving full-time support with current PNP technology is usually related to insufficient inspired volume generation. Moreover, even in tetraplegics who have achieved full time support via PNP, insufficient inspired volume generation remains a concern as it often restricts normal speech production.

Several factors may account for inadequate inspired volume production during PNP. First, peripheral nerve electrodes generally do not result in complete diaphragm activation due to the high thresholds of some axons. Second, there is lack of co-incident inspiratory intercostal/accessory (IC) muscle activation, a muscle group which is responsible for the generation of about 35-40% of the vital capacity. The lack of IC activation also prevents the synergistic interaction of combined IC and diaphragm activation to generate inspired volume and airway pressure. In fact, since the rib cage moves paradoxically inward during inspiration, PNP results in the performance of negative work. Finally, PNP is applied with low frequencies (<20 Hz) which converts skeletal muscle from a normally mixed fiber population (e.g. diaphragm is comprised of about 60% slow and about 40% fast fibers) to one comprised predominantly of slow fibers. While low frequency stimulation increases the endurance characteristics of electrically stimulated muscles, it also significantly reduces fiber diameter and maximum force generation. Consequently, the magnitude of maximum inspired volume generation is reduced. Chronic application of PNP with higher stimulus frequencies (>20 Hz) is not possible as this has been shown to result in diaphragm muscle fiber damage.

In patients with inadequate phrenic nerve function, attempts have been made to electrically activate the IC muscle group to provide these patients with an alternative method of pacing. For example, in dog studies it has been shown that the IC muscles can be activated via epidural upper thoracic ventral root stimulation (VRS). VRS results in marked contraction of the IC muscles including the parasternal and interrosseous muscles. Since the expiratory intercostal muscles in the upper portion of the rib cage are very thin, they generate a negligible opposing action. Optimal inspired volumes are generated with ventral electrode placement at the T2 spinal cord level with decreases in inspired volume production at sites above and below this level. Maximal electrical stimulation (6 mA, 50 Hz, 0.1 ms) with a single electrode results in large inspired volumes (about 35% of the vital capacity). In fact, stimulation of the IC muscles by VRS in combination with bilateral phrenic nerve stimulation, results in the generation of inspired volumes that represent about 80% of the inspiratory capacity. Moreover, animals can be ventilated by this method for prolonged time periods (6-8 hours without the development of system fatigue). The mechanism of inspiratory muscle activation by this method occurs via direct spread of current to the motor roots and does not involve stimulation of the spinal cord. Consequently, non-respiratory muscles innervated by the upper thoracic ventral roots are also activated by this technique. Side effects include contraction of the muscles of the upper extremity and trunk.

In clinical trials, this technique was applied in ventilator dependent tetraplegics with absent phrenic nerve function in an attempt to maintain artificial ventilation via IC muscle pacing alone. While VRS resulted in the generation of large inspired volumes (500-900 ml), ventilation could be maintained for only a few hours/day. There are a number of factors which limit the success of this technique. First, the application of chronic low frequency stimulation of the IC muscles reduced their fiber diameter and force generating capacity and, in turn, the magnitude of inspired volume generation. Second, the co-activation of non-respiratory muscles resulted in significant increases in metabolic rate and co-incident increases in ventilatory requirements. Non-respiratory muscle contraction also resulted in mild, but undesirable contraction of the upper extremity and trunk muscles, as seen in the prior animal studies.

In separate clinical trials, VRS was applied in four ventilator dependent patients with only unilateral phrenic nerve function. In these patients, it was demonstrated that artificial ventilation generated by combined IC muscle and unilateral phrenic nerve stimulation was sufficient to comfortably maintain ventilatory support, ranging from 16 hours/day to full-time. Inspired volumes achieved by combined pacing were in the range of that observed with bilateral PNP. This method also resulted in contraction of the upper trunk musculature and mild upper extremity motion, which was generally well tolerated. In some patients however, this movement interfered with certain activities involving fine motor control, such as use of a joystick by mouth control. Another disadvantage of this technique is that it requires two separate procedures for electrode implantation. Given these technical difficulties and the small patient population, this technique is not commercially viable.

Accordingly, current inspiratory muscle pacing techniques have provided many tetraplegics with freedom from mechanical ventilation and in some cases, complete independence. Recent developments have also provided minimally invasive methods of electrode placement for PNP and, potential pacing options for tetraplegics with only unilateral phrenic nerve function. However, these techniques have been successful in achieving full-time ventilatory support in only about 50% of patients. In addition, due to lack of phrenic nerve viability, a substantial number of ventilator dependent tetraplegics cannot be offered any form of pacing. Consequently, the vast majority of ventilator dependent tetraplegics still require the use of mechanical ventilation. The pacing options for ventilator dependent tetraplegics therefore remain quite limited and need to be expanded.

SUMMARY

Provided is a method of activating the inspiratory muscles in a subject having a spinal cord injury or progressive neurodegenerative disorder, comprising positioning one or more electrodes at one or more levels of the upper thoracic spinal cord of the subject; and operating the electrode to deliver a high frequency electrical stimulation to the spinal cord tracts at said level or levels.

According to certain illustrative embodiments, the method of activating inspiratory muscles in a subject comprising activating the inspiratory muscles in a subject having a neurodegenerative disease comprises positioning one or more electrodes at one or more levels of the upper thoracic spinal cord of the subject; and operating the electrode to deliver a high frequency electrical stimulation to the spinal cord tracts at said level or levels.

According to further illustrative embodiments, provided is a method of preserving function of inspiratory motorneurons in a subject with a spinal cord injury or progressive neurodegenerative disorder comprising periodically operating one or more electrodes at one or more levels of the upper thoracic spinal cord of the subject to deliver a high frequency electrical stimulation to the spinal cord tracts to activate the inspiratory muscles.

Additionally provided is a system for activating inspiratory muscles in a subject, the system comprising an electric signal generator; and an electrode coupled to the electrical signal generator, the electrode being configured to be positioned at one or more levels of the upper thoracic spinal cord of the subject and to deliver high frequency electrical stimulation emitted from the electric signal generator.

BRIEF DESCRIPTION OF THE DRAWINGS

FIG. 11 illustrates the experimental set-up to monitor leg movement during spinal cord stimulation. At conventional stimulus frequencies (50 Hz), there is considerable leg movement associated with the generation of an inspired volume of 400 ml. However, with high frequency spinal cord stimulation, there is virtually no leg movement.

DETAILED DESCRIPTION

A system and method are provided for activating the inspiratory muscles in a subject. The method of activating the inspiratory muscles in a subject includes positioning one or more electrodes at a desired level or levels on the upper thoracic spinal cord of the subject, and operating the electrode to deliver high frequency electrical stimulation to the spinal cord tracts at that level or levels. The method may be used to activate the inspiratory muscles in subjects suffering from spinal cord injuries or from neurodegenerative disorders.

The terms "spinal cord level" or "spinal cord levels" as used herein refers to the location(s) or point(s) where spinal roots forming each of the T1-T6 thoracic nerves emanate from the spinal cord. Stimulation of the spinal cord tracts that synapse with the phrenic, intercostal and accessory (scalene muscles and sternocleidomastoid muscles) motorneuron pools results in activation of the respiratory muscles in a much more physiologic manner as compared to directly stimulating the phrenic nerves, intercostal nerves or nerves to the accessory muscles. Thus, stimulating the appropriate spinal cord tracts results in a more physiologic and effective activation of each of the inspiratory muscles. Moreover, this method results in activation of the different inspiratory muscles in concert (i.e., substantially simultaneously).

A system for activating inspiratory muscles in a subject is also provided. The system includes an electric signal generator and at least one electrode coupled to the electrical signal generator. According to certain embodiments, the electric signal generator delivers electrical stimulation periodically. The electric signal generator may be operatively coupled to a radiofrequency transmitter. The electrode is configured to be positioned on or in a level of the upper thoracic spinal cord of the subject and to deliver high frequency electrical stimulation emitted from the electric signal generator. The system is configured to deliver an electrical stimulation having a frequency from about 100 hertz to about 500 hertz and a pulse amplitude from about 0.5 milliamps to about 50 milliamps. The electrode may comprise a unipolar, bipolar or tripolar stimulating electrode that is configured to be implanted either non-invasively through a wire, or via a laminectomy incision.

As used herein, the term "inspiratory muscles" refer to the muscles that are active during inspiration. The term "muscle activation" as used herein, refers to the contraction of muscle in response to stimulation by electrical impulses.

Figure 1:
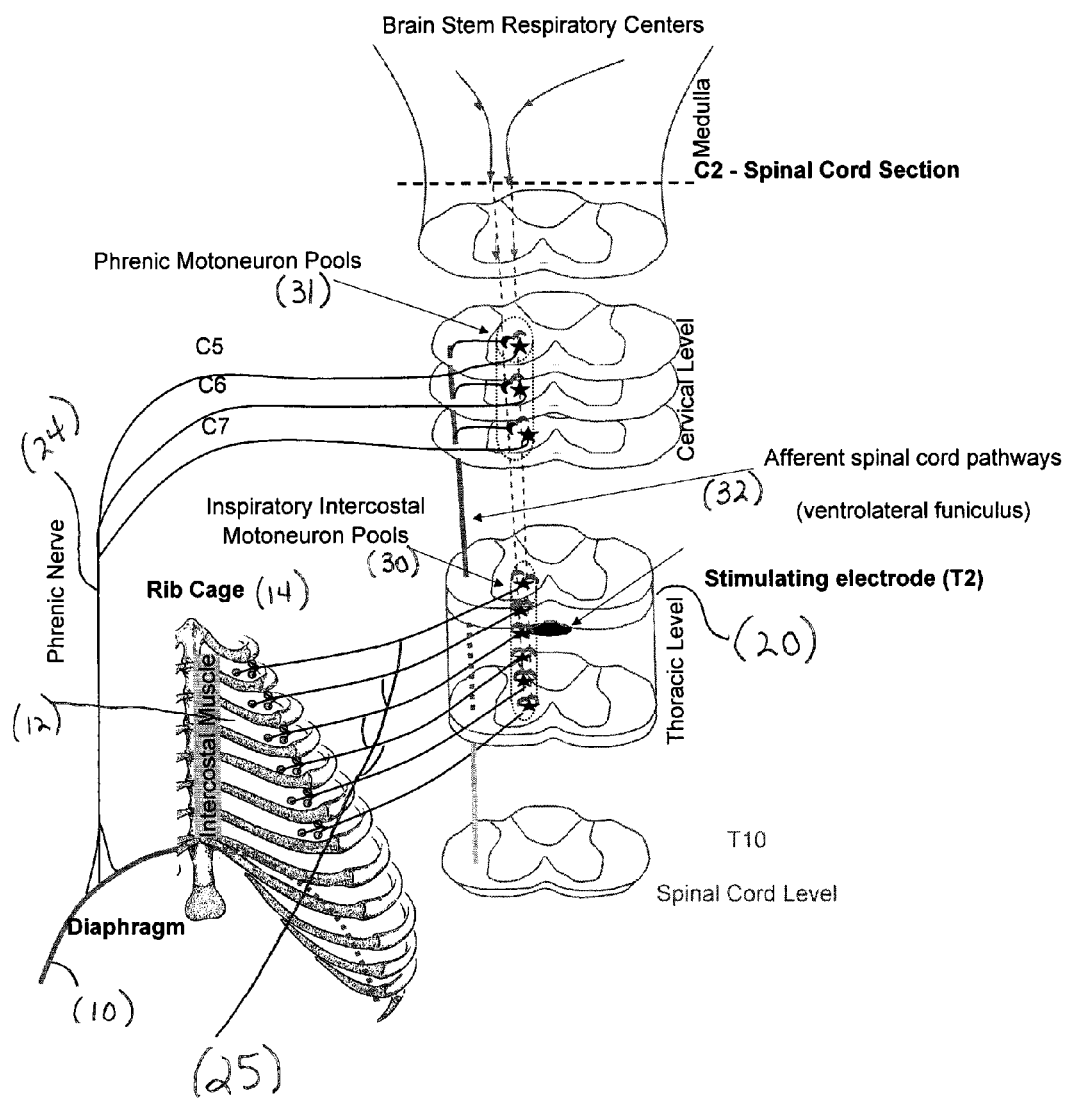
FIG. 1 is a schematic diagram of a stimulating electrode positioned at a spinal cord level and the nerve pathways extending from this spinal cord level to the diaphragm and the intercostal muscles.

Referring to FIG. 1, the inspiratory muscles include the diaphragm (10) and the external intercostal muscles (12). The thoracic diaphragm (10) is a sheet of muscle extending across the lower portion of the ribcage (14). When the diaphragm (10) contracts, it substantially shortens, increasing the volume of the thorax (14), expanding the lungs and creating a pressure differential that draws in air. There are other muscles, referred to as the intercostal muscles, which are located between the ribs and help form and move the chest wall. Activation of the external intercostal muscles (12) aids in the process of expanding the lungs by lifting and separating the ribs during inhalation. If the inspiratory muscles are weak or paralyzed, the lungs may not fully expand with each breath. The system and method provided herein activate the inspiratory muscles to cause inhalation.

The human spinal cord is divided into the cervical, thoracic, lumbar, sacral, and coccygeal levels. The cervical region provides activation signals to the thoracic diaphragm through the phrenic nerves. The thoracic region includes twelve levels, numbered T1-T12, of which T1-T6 are upper thoracic levels, and provides activation of the intercostal muscles through the intercostal nerves. According to certain embodiments, the method of activating inspiratory muscles includes positioning one or more electrodes at one or more levels of the upper thoracic spinal cord of a subject and operating the electrode to deliver high frequency electrical stimulation to the upper thoracic spinal cord tracts at the one or more levels.

The method includes the application of electrical current over the upper thoracic spinal cord (20) that synapses with inspiratory motorneuron pools, comprised of the intercostals motorneuron pools (30) and phrenic motorneuron pools (31), in order to activate both the diaphragm (10) and the external intercostal muscles (12) and accessory muscles. The method provides a more natural and physiological method of inspiratory muscle activation because stimulation occurs at a pre-motorneuron level, allowing processing of the stimulus within the motorneuron pools resulting in a more physiological pattern of activation. The term "physiological pattern of activation", as used herein, is an activation pattern which approximates or that is similar to that which occurs during spontaneous breathing in healthy individuals that are not suffering from respiratory dysfunction.

While not intending to be bound by theory, the more physiological pattern of activation, which includes activation of the diaphragm and external intercostal and accessory muscles, appears to be achieved as a result of the discharge patterns of the inspiratory motorneuron pools and excitatory reflex activation of the inspiratory motorneuron pools. Inspiratory motorneurons have been distinguished in terms of their onset of firing, as either early or late onset recruitment during a breath. While this can occur from differences in the central drive, there is evidence that all motorneurons in a given pool receive the same excitatory and inhibitory drive and that differences in excitability are due to differences in cell size and related variables. For a given synaptic current, the change in membrane potential experienced by the soma of a motorneuron is proportional to its input resistance. Since small motorneurons have the greatest input resistance, they experience the largest change in membrane potential for a given synaptic current and therefore reach threshold for the discharge of an action potential with less synaptic current. Consequently, variation in motorneuron size results in the recruitment of motor units in a sequential and in a specific hierarchical order. The smallest motor units, which activate slow fibers, are recruited first while larger units, which activate fast fibers, are recruited with increasing force requirements. According to the present method, high frequency spinal cord stimulation stimulates the motorneuron pools to generate a pattern muscle activation which resembles spontaneous breathing and thereby provides a more physiological breathing responses as compared to conventional methods of phrenic nerve stimulation.

While the inspiratory motorneuron pools are normally activated by descending bulbospinal tracts from the medulla, they also receive modulating inputs from several peripheral sources, including excitatory reflex effects. The order of motorneuron recruitment resulting from use of the method described herein results in spontaneous breathing in that small diameter axons and therefore smaller soma sizes are recruited before larger ones. The ascending pathways mediating the intercostal to phrenic reflex effects are located bilaterally in the ventrolateral funiculi (32), as shown in FIG. 1. In this method, it is believed that activation of the inspiratory motorneuron pools via high frequency spinal cord stimulation results from the stimulation of these previously described excitatory afferent tracts. Accordingly, stimulation of the upper thoracic region of the spinal cord can result in signals being sent to the phrenic nerve motorneuron pools (31) resulting in activation of the phrenic nerves (24). In support, it has been demonstrated that epidural electrical stimulation applied in the lower thoracic region results in diaphragm activation. DiMarco et al., Respir Physiol Neurobiol 159: 102-107 (2007). Reflex activation of the inspiratory motorneurons is demonstrated by the asynchronous EMG pattern resembling spontaneous muscle activation. As a result, electrical stimulation of the upper thoracic spinal cord can generate an asynchronous electromyogram signal in the diaphragm.

Other excitatory spinal cord tracts include the intercostal to intercostal excitatory tracts. These tracts are located bilaterally in the ventral portion of the spinal cord. In this method, it is believed that activation of the inspiratory motorneuron pools via high frequency spinal cord stimulation results from the stimulation of these previously described excitatory afferent tracts. Accordingly, stimulation of the upper thoracic region of the spinal cord can result in signals being sent to the intercostal motorneuron pools (30) resulting in activation of the intercostal nerves (25). Reflex activation of the inspiratory motorneurons is demonstrated by the asynchronous EMG pattern resembling spontaneous muscle activation. As a result, electrical stimulation of the upper thoracic spinal cord can generate an asynchronous electromyogram signal in the intercostal muscles.

The method of activating the inspiratory muscles can include delivering high frequency electrical stimulation to a spinal cord level. The external controlling circuitry of this transmitter is adjusted to provide timing parameters suitable for artificial respiration. The high frequency electrical stimulation can be provided in a variety of waveforms, such as sinusoidal, stepped, or trapezoidal waveforms, and can vary in terms of amplitude, frequency, timing, and pulse width. High frequency, as used herein, refers to frequencies of 100 hertz (Hz) and above. According to illustrative embodiments, high frequency electrical stimulation refers to frequencies greater than 200 Hz. According to other illustrative embodiments, the electrical stimulation may be provided with a frequency from about 200 Hz to about 500 Hz, while in other embodiments a frequency from about 200 to about 300 Hz may be used. The amount of current applied may range from about 0.1 milliamps (mA) to about 50 mA, with some embodiments using a range from about 1 mA to about 3 mA. Pulse amplitude can be varied between 0 and 40 V. Pulse width can be varied between 0.1 and 0.5 ms but should be maintained between 0.05 to 0.3 ms. Cycle on-time and off-time are adjusted to 0.5 to 1.8 seconds and 1 to 5.8 seconds, respectively. Pulse train rate (breaths per min) can be varied between 6 and 23. The pulse train rate may be established at about 7 to about 15 breaths/minute.

The method of activating inspiratory muscles also includes the steps of positioning one or more electrodes in or on a level of the upper thoracic spinal cord of a subject. A term "subject", as used herein, refers to a human or non-human animal, such as a domesticated farm animal (e.g., cow, horse, pig) or pet (e.g., dog, cat, etc). The upper thoracic spinal cord includes spinal cord segments T1, T2, T3, T4, and T5. Electrode placement results in the application of electrical current epidurally over the upper thoracic spinal cord. The electrodes can be positioned in or on one or more of these segments. In certain embodiments, the electrode is positioned in or on the T2 segment of the upper thoracic spinal cord. In order to determine the most effective segment or segments for receiving spinal cord stimulation for particular individuals or species, the spinal cord and surrounding tissue can be evaluated to determine the position for electrode placement using techniques known to those skilled in the art. See for example the discussion of electrode placement in U.S. Pat. No. 5,999,855, the disclosure of which is incorporated herein by reference.

Electrodes for spinal cord stimulation can be inserted percutaneously into or onto the nerves or close to the nerves or spinal cord region. Alternatively, the electrodes can be placed via a laminectomy or hemi-laminectomy incision onto the epidural surface of the spinal cord. The electrodes are positioned either at a level or levels of the upper thoracic spinal cord. The electrode may be positioned either on the dorsal or ventral surface of the upper thoracic spinal cord. The electrodes can be placed anywhere within the region near the target spinal cord segments. The electrode(s) may be introduced into the epidural space of the upper thoracic spinal cord either by a percutaneous approach or by surgical laminectomy or laminotomy. In some embodiments, electrodes that can be implanted less invasively, e.g., through a large bore needle by percutaneous means, can be used in order for implantation to be carried out in a relatively non-invasive fashion.

Figure 2:
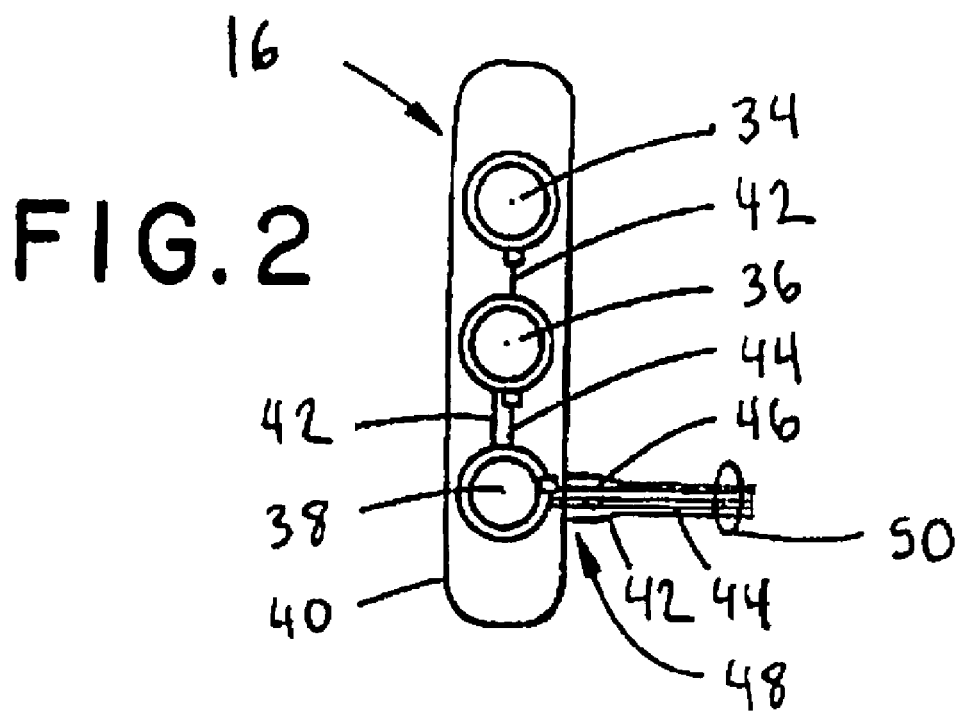
FIG. 2 is a schematic of an electrode that may be positioned surgically via a laminectomy near an upper thoracic spinal segment in order to electrically stimulate the spinal cord.

A variety of electrodes are suitable for providing electrical stimulation to segments of the upper thoracic spinal cord. For example, commercially available disc spinal cord electrodes (e.g., Medtronic #3586; 4 millimeter) can be used (FIG. 2). In some embodiments of the invention, a tripolar stimulating electrode can be used.

With specific reference to FIG. 2, a stimulating disc electrode (16) shown is a modified version of a standard electrode manufacture by Medtronic™ for use in their spinal cord stimulation (SCS) system. In the electrode (16) illustrated, three electrode plates (34), (36) and (38) are disposed in a silicon rubber insulating body portion (40). Each of the electrode plates (34), (36) and (38) are made from a platinum/iridium or pure platinum composition and are collinearly spaced apart on the body (40) as illustrated. A spacing distance of about 9 mm between each electrode plate center can be used.

In order to establish an optimal stimulation transfer, each of the electrode plates (34), (36) and (38) are of uniform size and construction. The cross-sectional diameters of each of the electrode plates may be 4.5 mm. The overall length and width of the insulating silicon rubber body (40) may be 35 mm and 7.5 mm respectively, although any suitable length and width may be determined by one having ordinary skill in the art.

The electrode 16 illustrated in FIG. 2 can be placed onto the ventral or dorsal surface of the spinal cord of a subject via a laminectomy incision. Connecting wires are attached to the leads forming the bundle (50) that forms an extension for connection to a demodulator circuit. The anode of the spinal cord electrode is preferably located several centimeters distal to the cathode located on the surface of the spinal cord. In that orientation a broad electric field is generated. The broad electric field induces electrical activity in the spinal cord effecting inspiratory muscle stimulation. The center of the electrode is positioned in the midline over this region of the spinal cord. The electrode can be positioned in the midline under fluoroscopic guidance to provide inspiratory muscle activation.

The method of activating inspiratory muscles by electrical stimulation can generate the inspired volume in a subject suffering from respiratory dysfunction. For example, it can result in an inspired volume of up to about 80% of the inspiratory capacity. The actual lung volume varies among subjects. The total lung capacity for an adult human, which is the volume of gas contained in the lung at the end of maximal inspiration, is typically about 6 liters. Importantly, this method of high frequency spinal cord stimulation can provide ventilation for prolonged periods of time, such as, for example, from 18 hours a day up to 24 hours a day.

In some embodiments, the electrical stimulation can be delivered periodically. This may be done, for example, to prevent hypoventilation or to facilitate breathing in conjunction with a mechanical ventilator. In embodiments of the method in which a ventilator is also used, the method can also include the step of delivering breathing gas from a ventilator to the subject, at least a portion of which is inhaled upon activation of the inspiratory muscles. In some cases, it may also be preferable to synchronize the delivery of breathing gas from the ventilator with the delivery of electrical stimulation by the electrode to provide breathing primarily when inhalation occurs in response to electrical stimulation.

Figure 3:
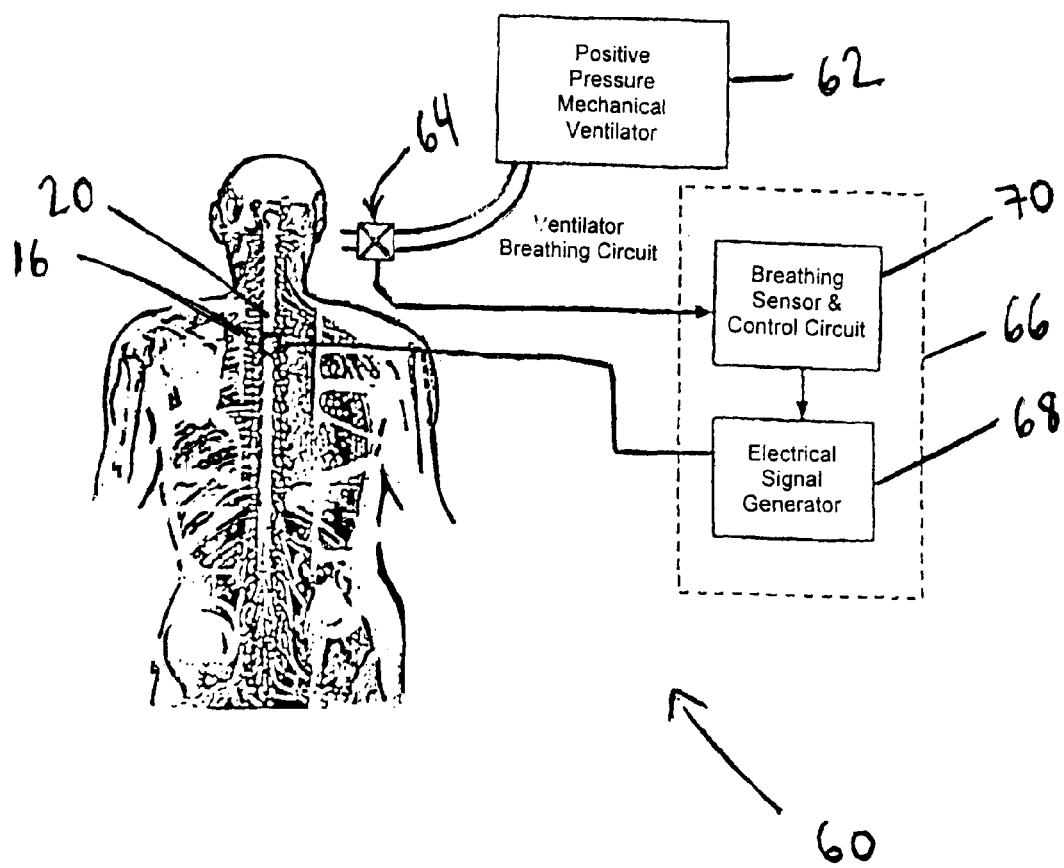
FIG. 3 is a schematic diagram of a system for activating inspiratory muscles in a subject that can optionally include positive pressure provided by a mechanical ventilator.

Another embodiment of the method provides a system for activating inspiratory muscles in a subject that includes an electric signal generator (68) and an electrode (16) coupled to the electrical signal generator as shown in FIG. 3. The electrode is configured to be positioned on or in a level of the upper thoracic spinal cord of the subject and to delivery high frequency electrical stimulation emitted from the electric signal generator.

An electrical signal generator (68) governs the signal delivered by the electrode (16). Depending on its size, the electrical signal generator (68) can be placed together with the electrode (16), or it may simply be in communication with the electrode (16). A variety of suitable electrical signal generators (68) are available. Non-limiting examples include a modified Finetech electrical stimulator, with parameter ranges of 0-40 volts, 10-600 Hz, and 0.1-1 millisecond pulse width.

The electrode (16) can include a battery to power the system, which can be a conventional or a rechargeable battery. The electrodes (16) can also use a radio frequency (RF) wireless connection such that the electric signal generator (68) is operatively coupled to a radio frequency transmitter. In these RF systems, a receiver device can be implanted subcutaneously and a transmitter is worn on the outside of the body. In this type of system, the electrode may not require its own battery. The antenna are tuned to each other and aligned such that control information and power is transmitted to the receiver, which then directs the electrical impulses to the electrodes through the leads. The external transmitter contains batteries to power the transmission. All systems have the capability to externally adjust settings of the electrode through a programming device.

FIG. 3 illustrates an embodiment of a system (60) for activating inspiratory muscles in a subject. The system (60) can be used in conjunction with a mechanical ventilator (62), as shown, or it can be used alone without a mechanical ventilator (62). The system for activating inspiratory muscles in a subject includes an electric signal generator; and an electrode coupled to the electrical signal generator, the electrode being configured to be positioned on or at a level of the upper thoracic spinal cord of the subject and to delivery high frequency electrical stimulation emitted from the electric signal generator. The system (60) can be used for subjects with acute ventilatory needs alone to provide breathing, or it can be used in conjunction with mechanical ventilation. In such an embodiments, the combined use of high frequency spinal cord stimulation and mechanical ventilation can increase tidal volume and/or to decrease maximal lung pressure in a lung during inspiration.

According to some embodiments, the system (60) can also include a flow sensor (64). The flow sensor (64) can be positioned along the ventilation breathing circuit (i.e., between the mechanical ventilator (62) and the upper airway of the subject). The flow sensor (64) can be used to sense inspiratory or expiratory airflow in the ventilator circuit.

In one embodiment, the system (60) can include a stimulation apparatus (66) that can include an electrical signal generator (68) (similar to the one described above) and a breathing sensor and control circuit (70) that is in electrical communication with the electrical signal generator (68) and the flow sensor (64). The breathing sensor and control circuit (70) can be configured to detect certain breathing attributes of the subject (e.g., the inspiration phase of a breath, the duration of the inspiration phase, the exhalation phase of a breath, the duration of the exhalation phase, tidal volume, and/or flow rate) convert these attributes to signals, and communicate these signals to the electrical signal generator (68). The electrical signal generator (68) then sends a signal to the one or more electrodes (16) positioned on the upper thoracic spinal cord (20). The electrical signal generator (68) can thus be configured to cause the electrodes (16) to provide electrical stimulation periodically.

Optionally, for systems providing mechanical ventilation together with electrical stimulation, the system (60) can include a pressure gauge (not shown) and gas meter (not shown) along the ventilator breathing circuit to measure the pressure and gas-related parameters of the subject's breathing, respectively. Also, a physiological measurement unit can be connected to the subject to measure certain physiological parameters such as blood pressure, blood values, body temperature, etc.

In one embodiment, electrical stimulation of the inspiratory muscles can be synchronized with attempts at breathing or breathing made by the subject (e.g., on the subject's own or by the mechanical ventilator). For example, electrical stimulation can be triggered following the inspiration phase of the breath (i.e., during exhalation) to maximize the contraction during the period when the diaphragm is at its longest length.

Another aspect of the method provides a method for treating respiratory dysfunction in a subject in need thereof that includes the steps of periodically operating one or more electrodes on or at a level of the upper thoracic spinal cord of the subject to deliver high frequency electrical stimulation to the spinal cord segment to activate the diaphragm, intercostal and accessory muscles. Respiratory dysfunction, as used herein, is a condition where there is insufficient inspiratory muscle force generating capacity to maintain ventilatory requirements and blood gas homeostasis. The term "treating", as used herein, refers to a partial or complete amelioration of dysfunction, and can be either temporary or permanent. Respiratory dysfunction can be treated entirely through electrical stimulation, or it can also include the step of delivering breathing gas from a ventilator to the subject, at least a portion of which is inhaled upon activation of the diaphragm and intercostal muscles.

Respiratory dysfunction and its management in spinal cord injury are described by Brown et al. (Brown et al., Respir. Care, 51(8), 853-870 (2006), the disclosure of which is incorporated herein by reference. Respiratory dysfunction that can be treated by embodiments of the method can occur as a result of a variety of conditions, such as amyotrophic lateral sclerosis, muscular dystrophy, stroke, drug overdose, brain injury, or spinal cord injury. The method can also be used to treat subjects that have suffered a partial or complete loss of phrenic nerve function. While loss of phrenic nerve function can decrease the response of the diaphragm to electrical stimulation, the method still provides electrical stimulation to the other inspiratory muscles and therefore can continue to provide treatment for such subjects.

The proposed method of inspiratory muscle activation is unique in several respects, one of which is that various inspiratory motorneuron pools may be activated with one or more electrodes and therefore a single stimulus paradigm. If the phrenic, inspiratory intercostal and accessory motorneuron pools are not each sufficiently activated, electrical stimulation may result in paradoxical inward motion of one portion of the chest wall and loss of potential synergism of combined intercostal and diaphragm contraction.

The method of activation the inspiratory muscles by high frequency spinal cord stimulation (HF-SCS) will be further described by reference to the following experiments. These experiments are offered to further illustrate the various embodiments of the method. It should be understood however, that various modifications may be made while remaining within the scope of the present method.

1. Determination of Optimal Stimulus Paradigm During HF-SCS

The evaluation of high frequency spinal cord stimulation (HF-SCS) was performed with electrode positioning at the T2 spinal cord level on the ventral surface of the spinal cord segment. A wide range of stimulus frequencies was explored over a range of stimulus currents. Electrical stimulation was applied with a 4 millimeter (mm) disc electrode positioned epidurally via a laminotomy incision.

Figure 4A:
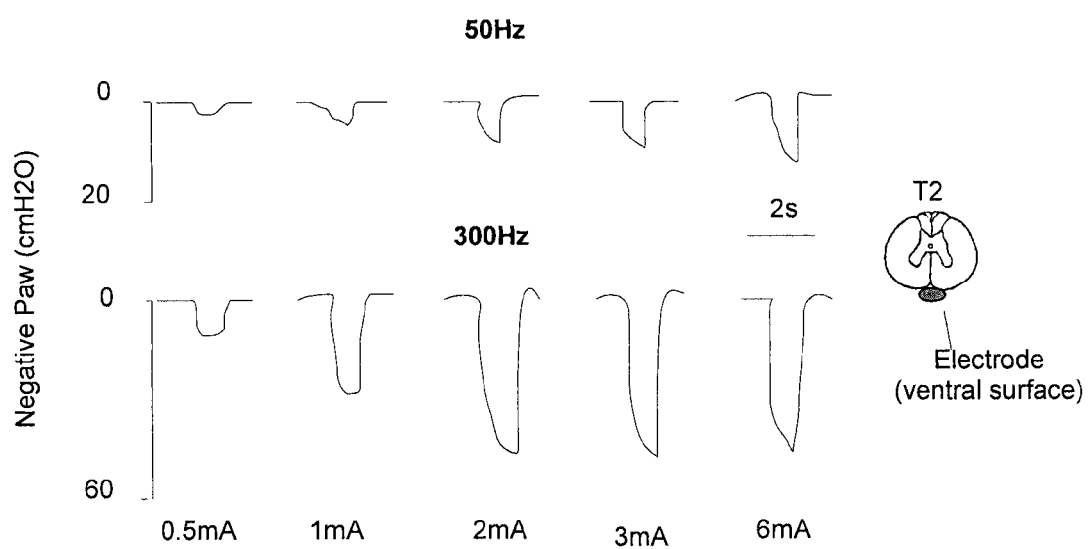
FIG. 4A shows raw data collected in an animal study demonstrating inspired volumes (ml) and negative airway pressures ($cmH_2O$) generated as a function of stimulus amplitude (0.2 ms pulse width) at conventional and high stimulus frequencies.

Inspired volumes and negative airway pressures generated as a function of stimulus amplitude (0.2 millisecond (ms) pulse width) at various stimulus frequencies were obtained. The evaluation was limited to stimulus currents of 6 milliamp (mA) since higher levels resulted in substantial body movement, in this particular preparation. Raw data from one animal subject was obtained in which the effects of 50 hertz (Hz) stimulation vs. 300 Hz stimulation (at the same stimulus current) were compared. As shown in FIG. 4A, at any given level of current, airway pressure generation was substantially larger at a frequency of 300 Hz compared to 50 Hz.

Figure 4B:
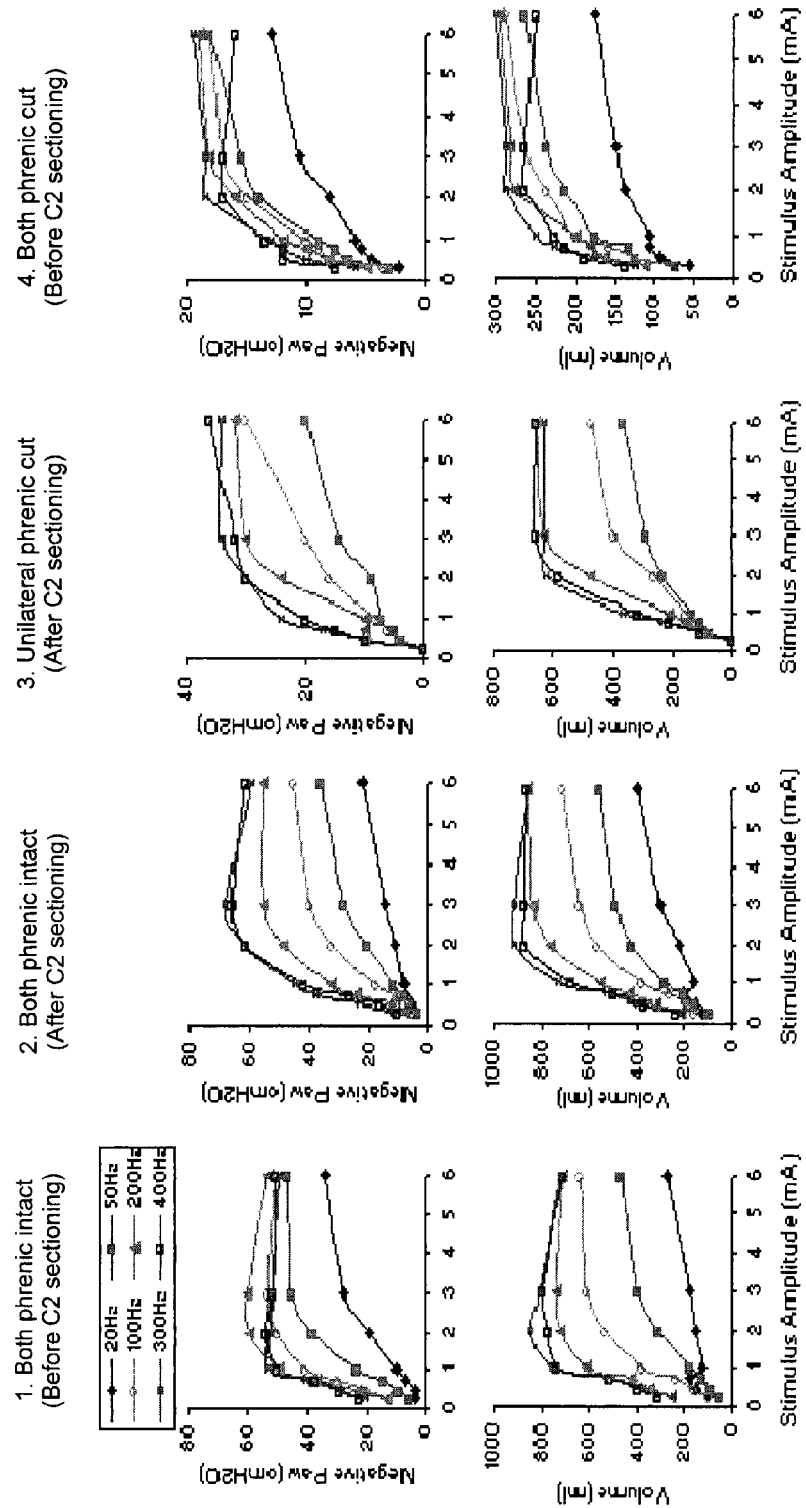
FIG. 4B compares raw data collected for inspired volumes (ml) and negative airway pressures ($cmH_2O$) generated as a function of various stimulus amplitudes and frequencies for subjects with both phrenic nerves intact (before and after cervical spinal cord sectioning), with unilateral phrenicotomy (after cervical sectioning), and with bilateral phrenicotomy (after cervical sectioning).

Data collected before and after C2 section, following unilateral phrenic nerve section and following bilateral phrenic nerve section were obtained and shown in FIG. 4B. Prior to phrenicotomy, inspired volume and airway generation increased with increasing stimulus amplitude. With conventional stimulus frequencies (20-50 Hz), these parameters were substantially smaller than that achieved with higher frequencies (>200 Hz). Maximum inspired volume and airway pressure were 920 ml and −72 cm $H_2O$, respectively. In addition, these maximum values were achieved at much lower levels of current (about 2 mA) during high frequency stimulation. In other studies, stimulus frequencies greater than 300 Hz did not result in greater output parameters. These values compare with maximal bilateral phrenic nerve stimulation (cuff electrode on each nerve, about 1 mA) which results in inspired volumes of about 400 milliliters (ml) and airway pressures of about 44 centimeters (cm) $H_2O$, from previous dog studies.

The inspiratory capacity of these animal subjects, as determined by passive inflation with a volume syringe to +30 cm $H_2O$, was about 1 liter. The high values achieved with HF-SCS, therefore, demonstrate near maximum activation of the diaphragm and intercostal muscles. It should be noted that output parameters are somewhat larger following C2 section, possibly related to inhibitory supraspinal influences present in the intact preparation. Qualitatively similar results were obtained following unilateral and bilateral cervical phrenicotomy. Phrenicotomy resulted in decreases in inspired volume and airway pressure generation. In each of these examples, maximum output parameters were also achieved at high stimulus frequencies (300 Hz) and low stimulus amplitudes (about 2 mA). Use of conventional stimulus frequencies (20-50 Hz) resulted in the generation of smaller inspired volumes and airway pressures at all stimulus amplitudes.

2. Evaluation of Optimal Electrode Location

Studies were also performed to evaluate the effects of electrode location on inspired volume and airway pressure generation. The effects of HF-SCS (300 Hz, 3 mA, 0.2 ms) over the epidural ventral surface of the upper thoracic spinal cord were evaluated in one animal subject. The greatest changes in output parameters were observed during stimulation at the upper thoracic T2 spinal cord segment. While there were only modest reductions in these parameters at more rostral spinal cord levels, there were marked reductions in these parameters at more caudal levels, possibly secondary to coincident expiratory muscle activation.

3. Analysis of the Pattern of Inspiratory Muscle Activation by EMG Recordings

Figure 5A:
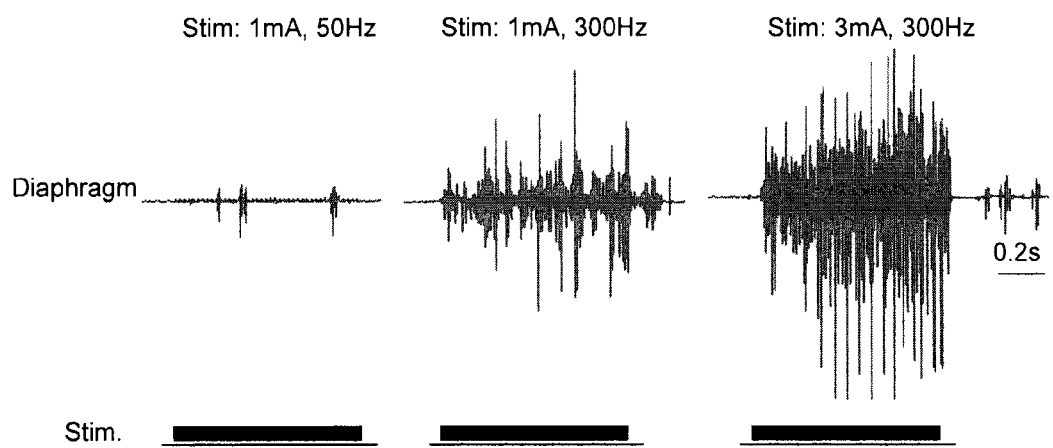
FIG. 5 includes views of electromyography (EMG) recordings; 5A shows the effects of increasing stimulus amplitude and frequency on the diaphragm EMG; 5B shows the EMGs of the parasternal and external intercostal muscles and costal diaphragm. For comparison the effects of direct phrenic nerve stimulation of the diaphragm in shown in FIG. 5C. A single action potential follows each stimulus spike which stands in contrast to the more physiologic asynchronous EMG resulting from high frequency stimulation (FIGS. 5A and 5B).

The pattern of activation of the various inspiratory muscles during HF-SCS was examined by analysis of their respective EMGs. In FIG. 5A, the effects of increasing stimulus amplitude and frequency on diaphragm EMG are provided. With a stimulus frequency of 50 Hz and 1 mA, there was minimal diaphragm activation. Increasing stimulus frequency to 300 Hz however resulted in marked motor unit recruitment. Increases in stimulus current to 3 mA at 300 Hz, resulted in further increases in the discharge pattern, most likely representing an increase in motor unit firing frequency and additional motor unit recruitment.

Figure 5B:
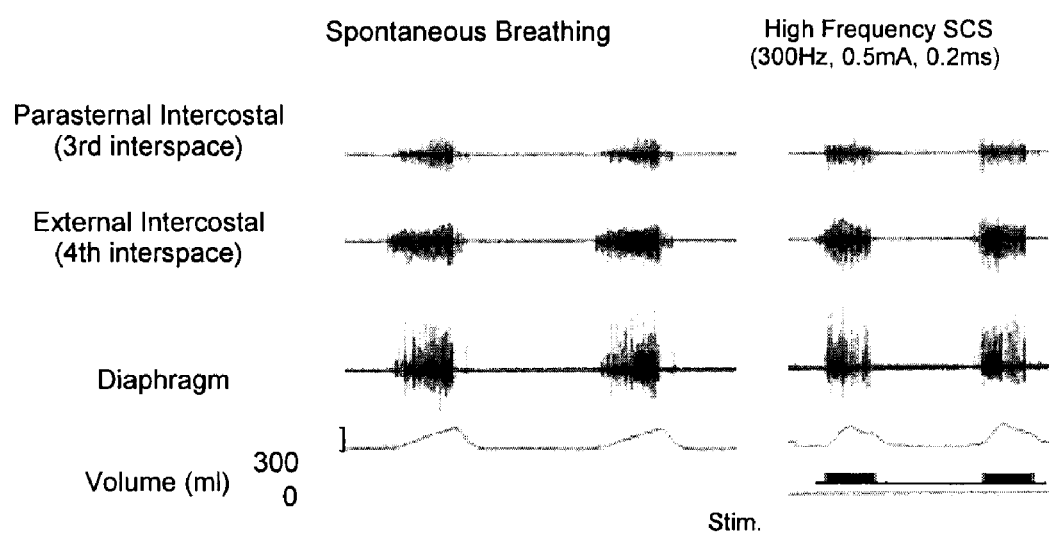

The EMGs of the parasternal and external intercostal muscles and costal diaphragm are provided in FIG. 5B. EMGs obtained during spontaneous breathing and during HF-SCS (300 Hz) with modulation of the stimulus current (0.5 mA) to generate a comparable inspired volume are shown. As with spontaneous breathing, HF-SCS generates an asynchronous EMG pattern in each of these inspiratory muscles. By contrast, direct phrenic nerve stimulation of the diaphragm and VRS of the intercostal muscles, as with all motor nerve stimulation techniques, results in synchronous activation of all axons. This is reflected in the single action potential following each stimulus spike (FIG. 5C). It should also be noted that the EMG pattern in response to HF-SCS persists for 100-200 ms following termination of the electrical stimulus, which is consistent with the development of plateau potentials.

4. Analysis of the Pattern of Inspiratory Muscle Activation: Single Motor Unit (SMU) Recordings.

Further analysis of neural output from the inspiratory motorneuron pools in response to HF-SCS was undertaken by recording SMU activity from the inspiratory muscles. Recording electrodes were placed in the costal diaphragm, external intercostal (3rd interspace), parasternal (3rd interspace) and scalene muscles. SMUs were identified by their specific shape characteristic. In response to HF-SCS (300 Hz, 1 mA), three separate motor units are readily identified by their specific shape characteristics. Each of the three SMUs obtained had similar morphology. In this instance, firing frequencies ranged between 8-10 Hz.

Figure 6:
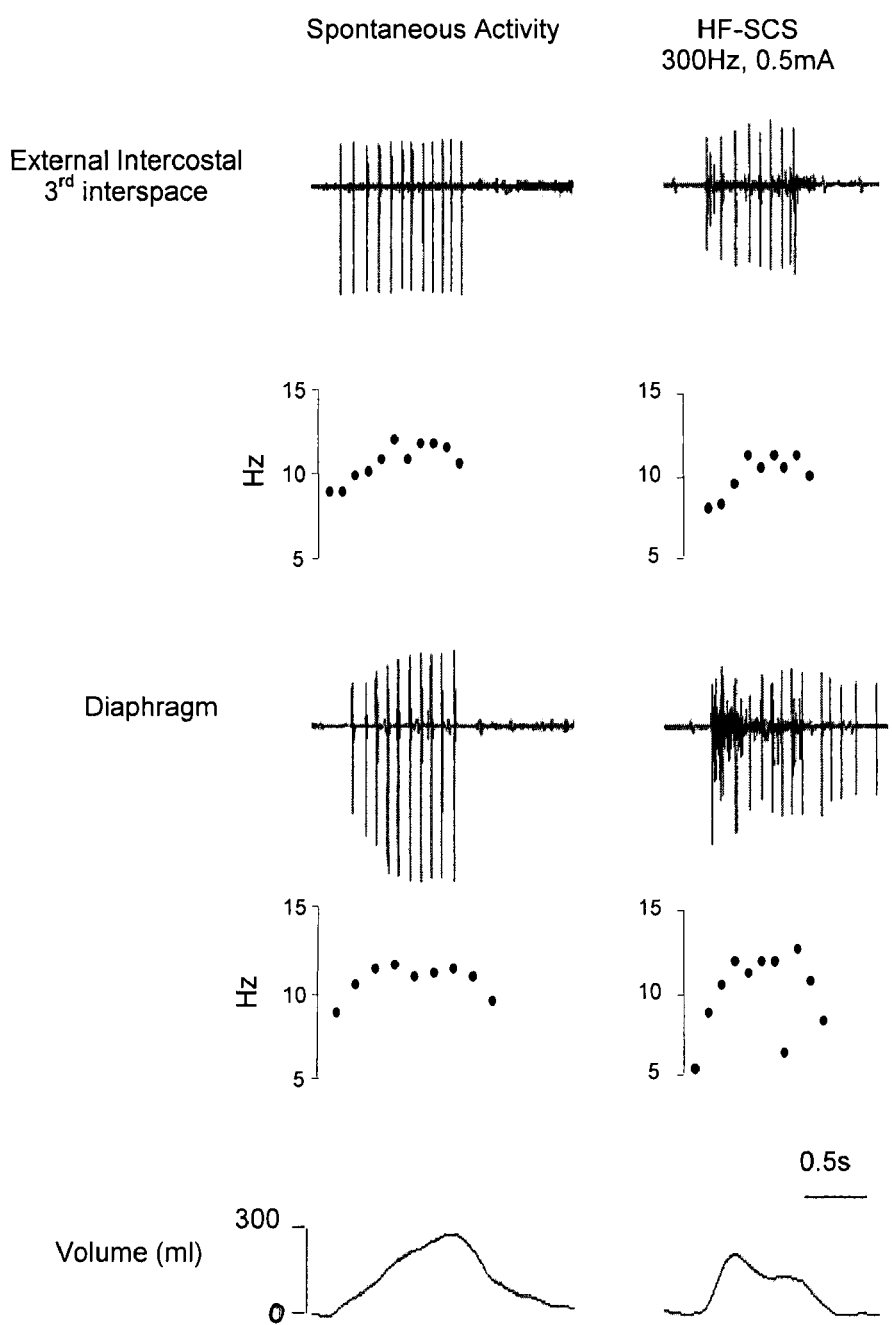
FIG. 6 includes a left panel that shows the single motor units (SMUs) and plots of their firing frequencies during spontaneous breathing for the diaphragm and external intercostal muscles, while the right hand panel shows the SMUs during HF-SCS (at comparable inspired volumes). Spinal cord stimulation (SCS) at 300 Hz results in processing the signal at the level of the motorneuron pools. This results in activation of the diaphragm and intercostal muscles at physiologic firing frequencies.

The SMUs and plots of their firing frequencies for the diaphragm and external intercostal muscles during spontaneous breathing and HF-SCS are shown in FIG. 6. SMUs during HF-SCS (at comparable inspired volumes) are shown in the right-hand panel. The SMU firing frequency tends to increase during the early portion of the breath, plateau and then decrease during the latter portion of the breath. The range of firing frequencies during HF-SCS is quite similar to that observed during spontaneous breathing. The range of SMU firing frequencies observed in our preliminary studies is also similar to published values of the same during spontaneous breathing, as shown in Table 1.

TABLE I

| Inspiratory Muscle | Spontaneous Breathing | High Frequency SCS |
|---|---|---|
| Diaphragm | 4.8-11.0 Hz[1] | 4.0-15.9 Hz |
| External Intercostal | 6.0-11.9 Hz[2] | 4.5-9.5 Hz |
| Parasternal Intercostal | 8.0-13.4 Hz[3] | 6.9-14.1 Hz |
| Scalene | 8.7-9.5 Hz[4] | 7.1-15.6 Hz |

[1]Butler et al., J. Physiol. 518, 3, pp. 907-920 (1999)
[2]De Troyer et al., J. Physiol. 546, 3, PP. 943-954 (2006)
[3]Gandevia et al., J. Physiol., 573, 1. PP. 263-275 (2006)
[4]Gandevia et al., Am. J. Respir. Crit. Care Med. 160, pp. 1598-1603 (2005)

Figure 7:
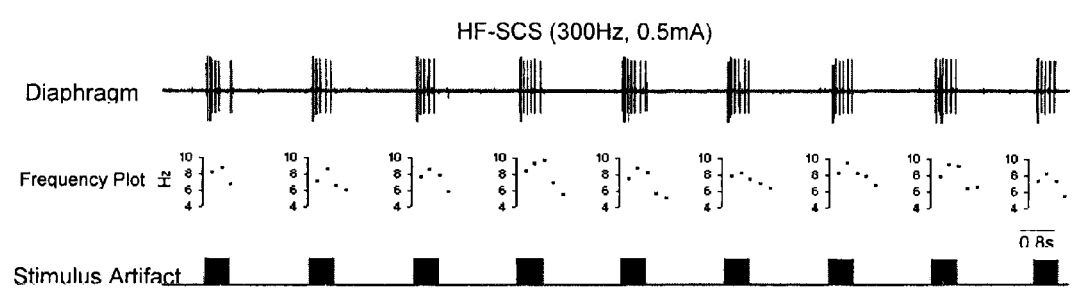
FIG. 7 illustrates the effects of repetitive stimulation (18 trains/min) on SMU firing frequency over a 30 s period. As shown, the firing frequency of a diaphragm SMU remains in the same physiologic range during repetitive HF-SCS.

While SMU recordings during single breath analysis resembled spontaneous breathing, it was not clear if this pattern would be sustained during repetitive stimulation. For example, repetitive HF-SCS could result in summation effects thereby altering the firing frequency of subsequent stimulus trains. Therefore, the effects of repetitive stimulation (18 trains/min) on SMU firing frequency were also evaluated over 30 seconds. This demonstrated that the firing frequency of a diaphragm SMU remains in the same physiologic range during repetitive HF-SCS, as shown in FIG. 7.

In summary, these results demonstrate that inspiratory motorneuron activation via HF-SCS allows processing of the stimulus within the motorneuron pools, resulting in a physiologic pattern of activation, remarkably similar to that which occurs during spontaneous breathing.

5. Determination of the Relative Participation of Diaphragm and Intercostal Muscle Contraction to Chest Wall Displacements.

Figure 8:
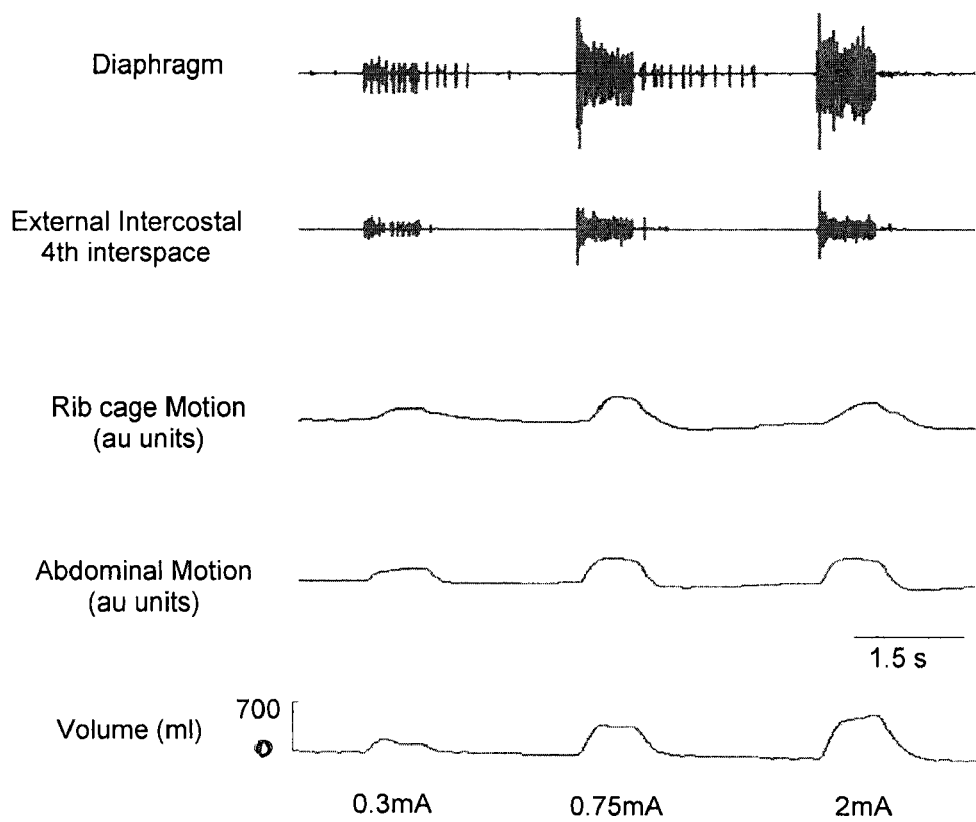
FIG. 8 shows the relative participation of the diaphragm and intercostal muscle contraction to chest wall displacements. EMGs, abdominal and rib cage motion, and inspired volume in an animal subject in response to the application of high frequency spinal cord stimulation at various stimulus intensities are displayed.

To evaluate the contribution of the rib cage and abdominal compartments during HF-SCS, rib cage and abdominal bands were placed circumferentially around the rib cage (at the mid portion of the sternum), and the abdominal wall (at the level of the umbilicus). The bands were calibrated during isovolume maneuvers by having the animal breathe against a closed airway. In addition tidal volume, intercostal and diaphragm EMGs were also monitored, for additional reference (FIG. 8). A range of inspired volumes (220, 430, and 730 ml) were achieved by modulating stimulation intensity (during HF-SCS, 300 Hz) and with $CO_2$ rebreathing (during spontaneous breathing). Inspiration at each lung volume is associated with synchronous expansion of both the rib cage and abdominal compartments. These results suggest that the distribution of inspiratory drive to the inspiratory intercostal and phrenic motorneuron pools was sufficient to maintain synchronous expansion of each compartment.

6. Localization of Spinal Cord Pathways Mediating Phrenic Motorneuron Activation During HF-SCS.

Figure 9:
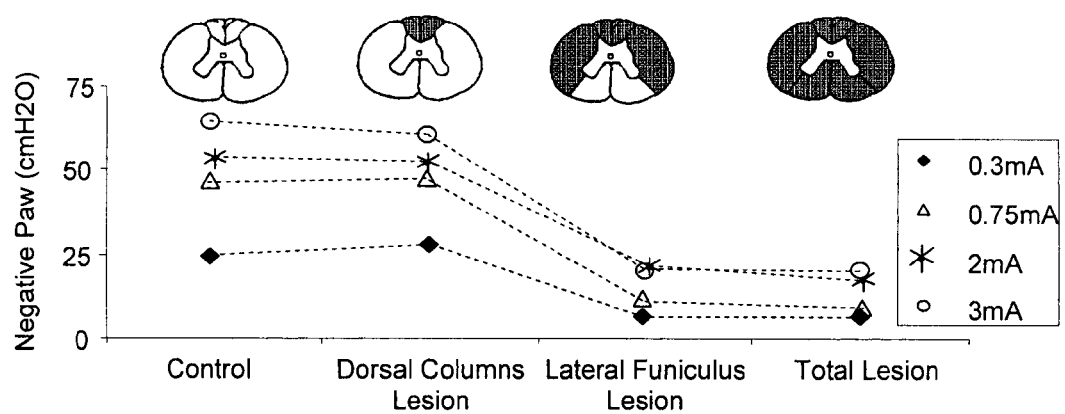
FIG. 9 shows the reduction in airway pressure generation in response to high frequency spinal cord stimulation before and after sequential spinal cord section at the C7 level.

A. Experiments were conducted to determine the location of pathways within the spinal cord by which the phrenic motorneuron pools are activated. HF-SCS (300 Hz) was provided before and after sequential spinal cord section at the C7 level (caudal to the phrenic motorneurons pools) in one animal. Stimulus amplitude was varied to provide a range of generated airway pressures. The results are reported in FIG. 9. The bilateral dorsal column section did not result in appreciable changes in inspired volume or airway pressure generation during stimulation. Following section of the lateral funiculi, however, there were marked reductions in airway pressure generation at all current levels. No further changes were noted following complete section of the spinal cord. The magnitude of airway pressure generation during HF-SCS following section of the lateral funiculi were similar to that achieved following bilateral phrenicotomy. These results suggest that the pathways mediating activation of the phrenic motorneuron pools are located in the lateral funiculi.

B. The existence of connections between the site of stimulation in the upper thoracic spinal cord and lower thoracic roots was also evaluated. SCS (single pulse, 0.5 mA, 0.2 ms) was applied at the T2 level while recording from the T10 dorsal root. A heavily anesthetized dog was paralyzed with curare to eliminate afferent input from contracting muscles. Single pulse stimulation resulted in an EMG response in the dorsal root with a latency of 2.1 ms. These results indicate that pathways within the field of stimulation in the upper thoracic spinal cord can be activated antidromicaly resulting in afferent recordings in the lower thoracic roots. These results show that the excitatory intercostal to phrenic reflex pathways play a role in mediating the observed responses during HF-SCS.

7. Determination of Pattern of Current Spread During SCS

Experiments were conducted to determine the pattern of current spread around the spinal cord. Using recording electrodes both above and below the area of stimulation (T2 level), the electric field was determined over the ventral surface of the spinal cord in one animal subject. Stimulation was performed with single stimulus (0.5 ms duration, 1.0 mA). Long pulses are necessary to achieve a steady state field and avoid artifacts. Measurements were taken every 0.5-1.0 cm in the rostral-caudal direction. The value of the electric field ($E=-\Delta V/\Delta X$) was determined by dividing the measured electrical potential difference ($\Delta V$) by the distance between the electrode wires ($\Delta X=0.5$ cm). The indifferent electrode was positioned cephalad to the stimulating electrode accounting for the asymmetric distribution of the electric field with larger values on the rostral compared to the caudal site. There is an exponential decrement in the magnitude of the electric field as a function of distance from the stimulating electrode. Within 6 cm of the stimulating electrode, the magnitude of the electric field fell to values below 5%. Based upon the measured threshold values, this data provides the stimulus current values necessary for direct ventral root activation. With optimal stimulation, current spread will be directed to the spinal cord pathways of interest with minimal direct activation of motor roots, the stimulation of which is likely to result in side effects, particularly unwanted contraction of non-respiratory muscles.

8. Efficacy of HF-SCS to Maintain Ventilation for Prolonged Periods

Figure 10:
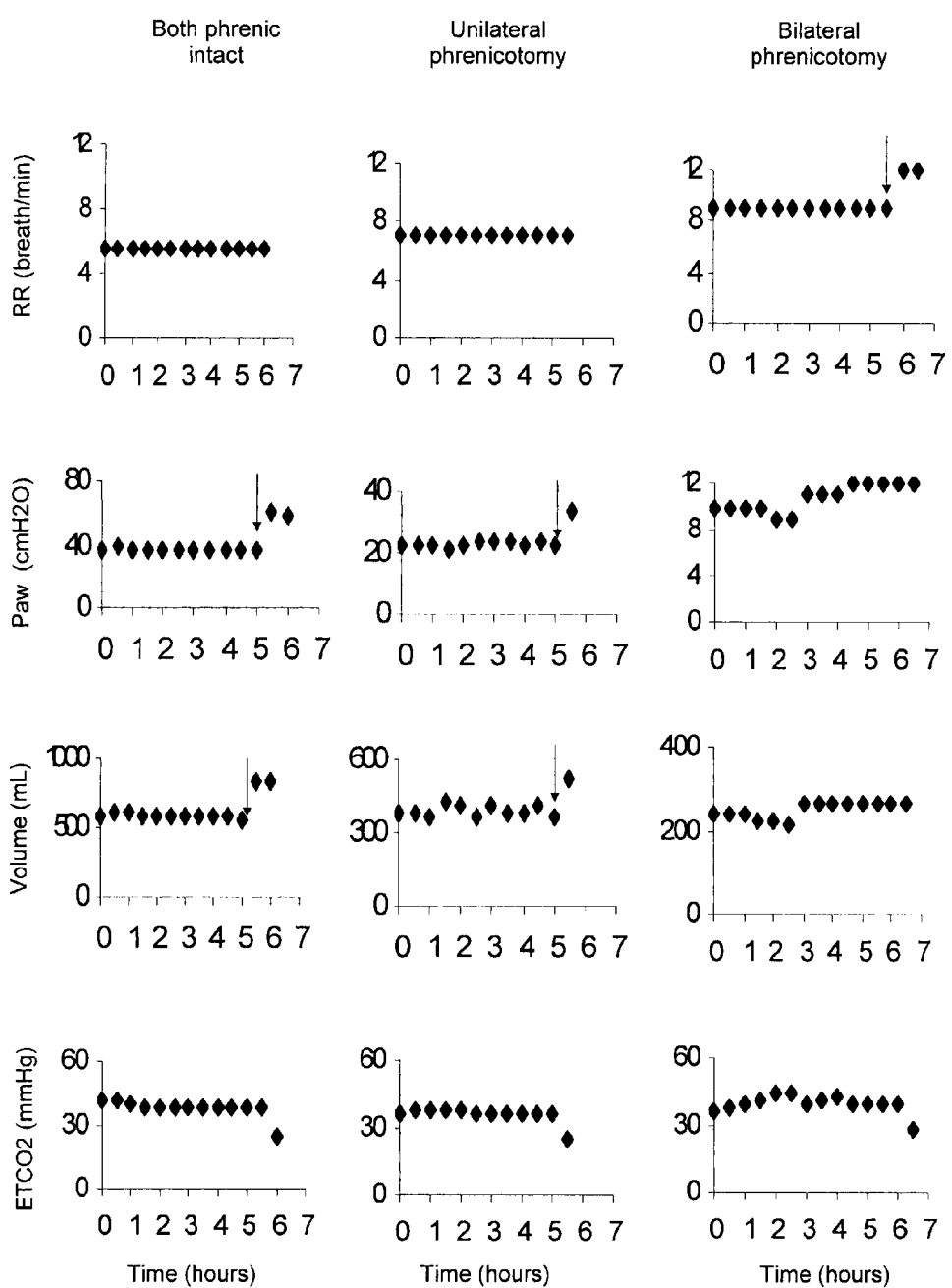
FIG. 10 demonstrates that inspired volume can be maintained for a minimum of 6 hours without the development of fatigue, by high frequency spinal cord stimulation. Importantly, $PCO_2$ levels are maintained in the normal range throughout. Moreover, ventilation can be maintained with high frequency spinal cord stimulation after unilateral and bilateral phrenicotomy.

The studies described above indicate that large inspired volumes can be generated by HF-SCS. The capacity of this method to maintain ventilatory support for prolonged periods was also evaluated. In anesthetized dogs, HF-SCS was applied to generate inspired volumes in the range of that occurring during spontaneous breathing. Stimulus amplitude was adjusted to achieve the desired inspired volumes. In animal studies inspired volume, airway pressure, $pCO_2$ and oxygen saturation were monitored during inspiratory muscle pacing for 6 hour periods. The studies were performed with HF-SCS (300 Hz) in a C2 preparation with phrenic nerves intact, and following unilateral phrenicotomy and bilateral phrenicotomy, in separate animal trials. These results are shown in FIG. 10.

In the C2 preparation, adequate inspired volumes could be generated with very low currents (0.5 mA, 0.2 ms); somewhat higher currents however were necessary in the unilateral phrenicotomy (1 mA, 0.2 ms) and bilateral phrenicotomy (1 mA, 0.2 ms) preparations. Under the three conditions, breathing rates were 5/min, 7/min and 9/min, respectively. Inspired volumes were maintained without significant change throughout the period of ventilatory support under each of the conditions. Importantly, $pCO_2$ values were maintained in the normal range, between 38-40 mm Hg as well. At the end of the intact phrenic and unilateral phrenicotomy trials, stimulus current was increased for 30 min. to 0.7 and 1.2 mA, respectively, resulting in periods of hyperventilation with $pCO_2$ values falling to 27 and 28 mmHg, respectively. In the bilateral phrenicotomy trial, breathing frequency was increased to 12 breaths/min. for 30 min.; this increase also resulted in a period of hyperventilation with $pCO_2$ values falling to 30 mm Hg. The results of these trials show that artificial ventilation can be maintained for prolonged periods with HF-SCS without the development of system fatigue. The results also indicate that the method can be used to effect artificial respiration in subjects with both phrenic nerves intact, with one phrenic nerve intact, or with no phrenic nerves intact.

9. Evaluation of Non-Inspiratory Muscle Activation and Movement During SCS.

The degree of forepaw flexion (joint angle movement) in an animal subject was monitored during HF-SCS and compared with movement resulting from VRS (50 Hz). Stimulus amplitudes were adjusted to result in similar inspired volumes. The experimental set-up is shown in FIG. 11. Upper extremity forepaw movements are shown is also shown. The 50 Hz paradigm was associated with marked flexion of the forepaw whereas there was minimal movement with the 300 Hz stimulus paradigm. Differences in the degree of forepaw movement are most likely secondary to the greater stimulus amplitude required with the 50 Hz paradigm. There was also substantial EMG activity in the triceps brachii, extensor carpi radialis and flexor carpi ulnaris muscles of the upper extremity with 50 Hz, but minimal activity with the 300 Hz paradigm. These results indicate that activation of inspiratory motorneuron pools by HF-SCS result in significantly less non-respiratory muscle contraction.

10. Evaluation of Expiratory Muscle Activation During HF-SCS.

In addition to the activation of the inspiratory motorneuron pools, the activation of the expiratory intercostal and upper portions of the abdominal muscles by HF-SCS was evaluated. In experiments in one animal, measurements of internal intercostal EMG were made during HF-SCS and compared to stimulation with conventional stimulus frequencies. External intercostal EMG from the same interspace was recorded for comparison. The application of the 300 Hz paradigm resulted in significantly greater external intercostal activation and inspired volume generation compared to the 50 Hz paradigm.

The magnitude of the EMG spikes of the internal intercostal muscle however was smaller during 300 Hz compared to 50 Hz stimulation. There was also significant intercostal EMG activity following termination of the stimulation suggesting post-inhibitory rebound. The mechanism of the differences between inspiratory and expiratory muscle activation consequent to alterations in stimulus frequency is not clear. It appears however that the high frequency stimulus paradigm is specific for activation of the inspiratory motorneuron pools whereas the expiratory muscles are activated by a different mechanism, possibly via direct motor root activation.

While the system and method for activating inspiratory muscles by high frequency spinal cord stimulation has been described above in connection with certain illustrative embodiments, it is to be Understood that other embodiments may be used or modifications and additions may be made to the described embodiments for performing the same function without deviating therefrom. Furthermore, all embodiments disclosed are not necessarily in the alternative, as various embodiments may be combined to provide the desired characteristics. Variations can be made by one having ordinary skill in the art without departing from the spirit and scope hereof. Therefore, the system and method should not be limited to any single embodiment, but rather construed in breadth and scope in accordance with the recitation of the attached claims.

The invention claimed is:

1. A method of activating inspiratory muscles in a subject having a spinal cord injury or a progressive neurodegenerative disorder comprising: positioning one or more electrodes at one or more levels of the upper thoracic spinal cord of the subject; and operating the electrode to deliver a high frequency electrical stimulation to the spinal cord tracts at said level or levels sufficient to activate the diaphragm and external intercostal muscles.

2. The method of claim 1 wherein activating the inspiratory muscles comprises simultaneously activating the diaphragm, the external intercostal muscles, parasternal intercostal muscles and accessory muscles.

3. The method of claim 1 comprising positioning the electrode at one or more levels of the upper thoracic spinal cord.

4. The method of claim 1 wherein positioning the electrode at said level of the upper thoracic spinal cord comprises positioning the electrode at the T2 level of the upper thoracic spinal cord.

5. The method of claim 1 comprising positioning the more than one electrode at a level of the upper thoracic spinal cord.

6. The method of claim 1 comprising positioning the more than one electrode at more than one level of the upper thoracic spinal cord.

7. The method of claim 3 wherein operating the electrode delivers an electrical stimulation having a frequency of 100 Hz or greater.

8. The method of claim 7 wherein operating the electrode delivers an electrical stimulation having a frequency of 200 Hz or greater.

9. The method of claim 8 wherein operating the electrode delivers an electrical stimulation having a frequency of about 200 Hz to about 500 Hz.

10. The method of claim 1 wherein the electrical stimulation has a pulse amplitude from about 0.1 milliamps to about 50 milliamps.

11. The method of claim 10 wherein the electrical stimulation has a pulse amplitude from about 0.5 milliamps to about 25 milliamps.

12. The method of claim 11 wherein the electrical stimulation has a pulse amplitude from about 0.5 milliamps to about 5 milliamps.

13. The method of claim 12 wherein the electrical stimulation has a pulse amplitude from about 0.5 milliamps to about 3 milliamps.

14. The method of claim 1 comprising operating the electrode to periodically deliver the electrical stimulation.

15. The method of claim 9 further comprising delivering breathing gas to the subject from a ventilator.

16. The method of claim 15 further comprising synchronizing delivery of the breathing gas from the ventilator with the delivery of electrical stimulation by the electrode.

17. The method of claim 1 comprising generating an asynchronous electromyogram signal in the diaphragm and the intercostal muscles by the electrical stimulation.

18. The method of claim 1 wherein the electrical stimulation causes an inspired volume up to about 80 percent of the inspiratory capacity of the subject.

19. The method of claim 1 wherein the electrical stimulation results in the development of an inspired volume sufficient to maintain adequate ventilation in the subject.

20. The method of claim 1 wherein the electrical stimulation causes sufficient activation of one or more of the inspiratory muscles to maintain the strength and/or endurance of the one or more of the inspiratory muscles.

21. The method of claim 20 wherein the inspiratory muscles comprise the diaphragm, external intercostal muscles, the parasternal intercostals muscles and the accessory muscles.

22. A method of preserving function of inspiratory motorneurons in a subject with a spinal cord injury or progressive neurodegenerative disorder comprising periodically operating one or more electrodes at one or more levels of the upper thoracic-spinal cord of the subject to deliver a high frequency electrical stimulation to the spinal cord tracts at said level or levels to activate the diaphragm and external intercostal muscles.

23. The method of claim 22 wherein activating the inspiratory muscles comprises activating the diaphragm, the external intercostal muscles, the parasternal intercostals muscles and the accessory muscles.

24. The method of claim 22 comprising positioning the electrode at one or more levels of the upper thoracic spinal cord.

25. The method of claim 22 wherein positioning the electrode at said level of the upper thoracic spinal cord comprises positioning the electrode at the T2 level of the upper thoracic spinal cord.

26. The method of claim 22 comprising positioning more than one electrode at a level of the upper thoracic spinal cord.

27. The method of claim 22 comprising positioning more than one electrode at more than one level of the upper thoracic spinal cord.

28. The method of claim 22 wherein operating the electrode delivers an electrical stimulation having a frequency of 100 Hz or greater.

29. The method of claim 28 wherein operating the electrode delivers an electrical stimulation having a frequency of 200 Hz or greater.

30. The method of claim 29 wherein operating the electrode delivers an electrical stimulation having a frequency of about 200 Hz to about 500 Hz.

31. The method of claim 22 wherein the electrical stimulation has a pulse amplitude from about 0.1 milliamps to about 50 milliamps.

32. The method of claim 31 wherein the electrical stimulation has a pulse amplitude from about 0.5 milliamps to about 25 milliamps.

33. The method of claim 32 wherein the electrical stimulation has a pulse amplitude from about 0.5 milliamps to about 5 milliamps.

34. The method of claim 33 wherein the electrical stimulation has a pulse amplitude from about 0.5 milliamps to about 3 milliamps.

35. The method of claim 22 comprising operating the electrode to periodically deliver the electrical stimulation.

36. The method of claim 30 further comprising delivering breathing gas to the subject from a ventilator.

37. The method of claim 36 further comprising synchronizing delivery of the breathing gas from the ventilator with the delivery of electrical stimulation by the electrode.

38. The method of claim 22, wherein comprising generating an asynchronous electromyogram signal in the diaphragm and the intercostal muscles by the electrical stimulation.

* * * * *